United States Patent
Gale et al.

(10) Patent No.: US 9,408,526 B2
(45) Date of Patent: Aug. 9, 2016

(54) TELESCOPIC SUPPORT

(75) Inventors: David Gale, Cambridgeshire (GB);
Adrian Cooper, Cambridgeshire (GB);
Keith Marshall, Bedfordshire (GB)

(73) Assignee: Freehand 2010 Limited, Guildford (GB)

( * ) Notice: Subject to any disclaimer, the term of this patent is extended or adjusted under 35 U.S.C. 154(b) by 892 days.

(21) Appl. No.: 12/399,721

(22) Filed: Mar. 6, 2009

(65) Prior Publication Data

US 2009/0269179 A1    Oct. 29, 2009

(30) Foreign Application Priority Data

Mar. 12, 2008    (GB) .................................. 0804633.6

(51) Int. Cl.
*A61B 1/00*    (2006.01)
*A61B 17/00*    (2006.01)

(52) U.S. Cl.
CPC .......... *A61B 1/00149* (2013.01); *A61B 1/00147* (2013.01); *A61B 34/00* (2016.02); *A61B 2017/00991* (2013.01)

(58) Field of Classification Search
USPC ............................... 74/89.12, 89.18; 600/102
See application file for complete search history.

(56) References Cited

U.S. PATENT DOCUMENTS

| | | | |
|---|---|---|---|
| 5,109,718 A * | 5/1992 | Gugel et al. ................. | 73/866.5 |
| 5,749,362 A | 5/1998 | Funda et al. | |
| 6,394,955 B1 | 5/2002 | Perlitz | |
| 7,001,332 B1 * | 2/2006 | Valentini et al. ............. | 600/210 |
| 7,447,537 B1 * | 11/2008 | Funda et al. ................. | 600/424 |
| 2005/0165271 A1 * | 7/2005 | Shioda et al. ................. | 600/102 |
| 2005/0234293 A1 * | 10/2005 | Yamamoto et al. ........... | 600/102 |
| 2007/0028532 A1 * | 2/2007 | Douglas et al. ............... | 52/118 |
| 2007/0137371 A1 | 6/2007 | Devengenzo et al. | |
| 2007/0137372 A1 * | 6/2007 | Devengenzo et al. ..... | 74/490.01 |
| 2007/0268540 A1 * | 11/2007 | Gaspardo et al. ............ | 359/201 |
| 2009/0048611 A1 * | 2/2009 | Funda et al. ................. | 606/130 |

(Continued)

FOREIGN PATENT DOCUMENTS

| WO | WO 2008/001003 A2 | 1/2008 |
|---|---|---|
| WO | WO 2008/001003 A3 | 6/2008 |

OTHER PUBLICATIONS

ASHCSP, Training Manual for Health Care Central Service Technicians, 2006, Jossey-Bass, Fifth Edition, pp. 104-111.*
Daniel H. Kim, Endoscopic Sine Procedures, 2011, Thieme, Ch. 2.*
Webster's New Collegiate Dictionary, 1974, G&C Merriam Company, p. 1001.*

(Continued)

*Primary Examiner* — Anhtuan T Nguyen
*Assistant Examiner* — Alexandra Newton
(74) *Attorney, Agent, or Firm* — Lewis, Reese & Nesmith, PLLC

(57) ABSTRACT

The present invention is a telescopic drive device of a device for holding a surgical instrument. The telescopic drive device includes a support; a first telescopic stage carried by the support; a first telescopic stage carried by the support, the first telescopic stage being able to perform a first motion with respect to the support; a second telescopic stage, which is able to perform a second motion with respect to the first telescopic stage; and a drive system, which is operable to drive the first and second motions. The first telescopic element performs the first motion and the second telescopic element simultaneously performs the second motion. The telescopic drive is operable to support a further device and to move the further device such that the movement is centered around a point or wherein each of the telescopic elements is arcuate.

19 Claims, 3 Drawing Sheets

(56) References Cited

U.S. PATENT DOCUMENTS

2009/0241705 A1* 10/2009 Subramanian et al. ...... 74/89.21
2009/0306754 A1* 12/2009 Parker et al. .................. 607/137

OTHER PUBLICATIONS

European search report and search opinion dated Jan. 13, 2014 for EP Application No. 09154606.9.

* cited by examiner

TELESCOPIC SUPPORT

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

This invention relates to a telescopic support, and in particular concerns a telescopic support for holding and/or manipulating a medical device.

2. Description of Related Art Including Information Disclosed Under 37 CFR 1.97 and 37 CFR 1.98.

There are several applications in which a drive is used to maneuver a carrier around a fixed point. An example of such an application is a robotic arrangement to hold a camera for use in endoscopy, where the endoscope is inserted into an incision in the body of a patient, and is then driven to move along or around two or more axes in such a way that the movement is confocal around the incision. This means that the endoscope may be moved with the point of the incision being the center of motion, so that the endoscope remains inserted into the incision and does not exert any substantial forces on the sides of the incision.

Confocal motion of this type often comprises pan, tilt, and zoom motions. During the "tilt" movement, the angle of the endoscope changes with respect to the surface of the patient's skin in which the incision is made.

In order to achieve tilt motion without exerting forces on the sides of the incision in the patient's body, an arcuate arm may be provided, having a radius of curvature which is centered on the incision. The endoscope is typically carried at one end of the arcuate arm, and it will be appreciated that driving the arcuate arm to describe a rotary motion about the incision, with all parts of the arm remaining at the same distance from the incision, causes the endoscope to tilt with respect to the patient, whilst remaining substantially motionless at the point where the endoscope passes through the incision.

Depending upon the application for which the endoscope is being used, however, the range of tilt motion that is required of the endoscope may be relatively large. To accommodate the positions of the endoscope that are required in various surgical operations, an endoscope may be required to be positioned in a substantially vertical orientation (i.e. perpendicular to the skin of the patient in which the incision is made), to a position which is a few degrees below horizontal (i.e. below the plane of the patient's skin in which the incision is made). In total, it is desirable for the endoscope to have a range of motion of around 110°.

If a solid arcuate arm is used however, it will be understood that this arcuate arm must cover at least 110° of arc in order to be able to support the endoscope in both of these end-of-range positions. This raises difficulties since, if the endoscope is moved to a substantially vertical position, the far end of the arcuate arm (i.e. the end furthest from the point at which the endoscope is supported) would travel sufficiently far along its arcuate path to press into the skin of the patient. Clearly, this is undesirable.

It is an object of the present invention to seek to ameliorate this difficulty.

BRIEF SUMMARY OF THE INVENTION

Accordingly, one aspect of the present invention provides a device for holding a surgical instrument, the device having a telescopic drive comprising a support; a first telescopic stage carried by the support, the first telescopic stage being able to perform a first motion with respect to the support; a second telescopic stage, which is able to perform a second motion with respect to the first telescopic stage; and a drive system, which is operable to drive the first and second motions, so that the first telescopic element performs the first motion and the second telescopic element simultaneously performs the second motion, wherein each of the telescopic elements is arcuate.

Preferably, each of the telescopic elements has a range of motion with respective ends, and wherein, starting from a position in which both telescopic elements are at one end of their respective ranges of motion, the drive system is operable to drive the telescopic elements simultaneously so that the telescopic elements reach the ends of their respective ranges of motion substantially simultaneously.

Preferably a third telescopic stage is provided, the third telescopic stage being adapted to perform third motion with respect to the second telescopic stage, and wherein the drive arrangement is configured to drive the third motion simultaneously with the first and second motions.

Conveniently, the endoscope is supported by the telescopic drive.

Preferably, the telescopic drive is operable to support a further device and to move the further device such that the movement is centered around a point.

Advantageously, the telescopic drive moves the further device in a tilt movement with respect to the point.

Conveniently, the further object may be moved along or around a plurality of axes to describe motion that is confocal about the point.

Advantageously, the device is a robot.

Accordingly, one aspect of the present invention provides a device for holding a surgical instrument, the device having a telescopic drive comprising a support; a first telescopic stage carried by the support, the first telescopic stage being able to perform a first motion with respect to the support; a second telescopic stage, which is able to perform a second motion with respect to the first telescopic stage; and a drive system, which is operable to drive the first and second motions, so that the first telescopic element performs the first motion and the second telescopic element simultaneously performs the second motion, wherein the telescopic drive is operable to support a further device and to move the further device such that the movement is centered around a point.

BRIEF DESCRIPTION OF THE SEVERAL VIEWS OF THE DRAWINGS

In order that the present invention may be more readily understood, embodiments thereof will now be described, by way of example, with reference to the accompanying drawings.

DETAILED DESCRIPTION OF THE INVENTION

Figure 1:
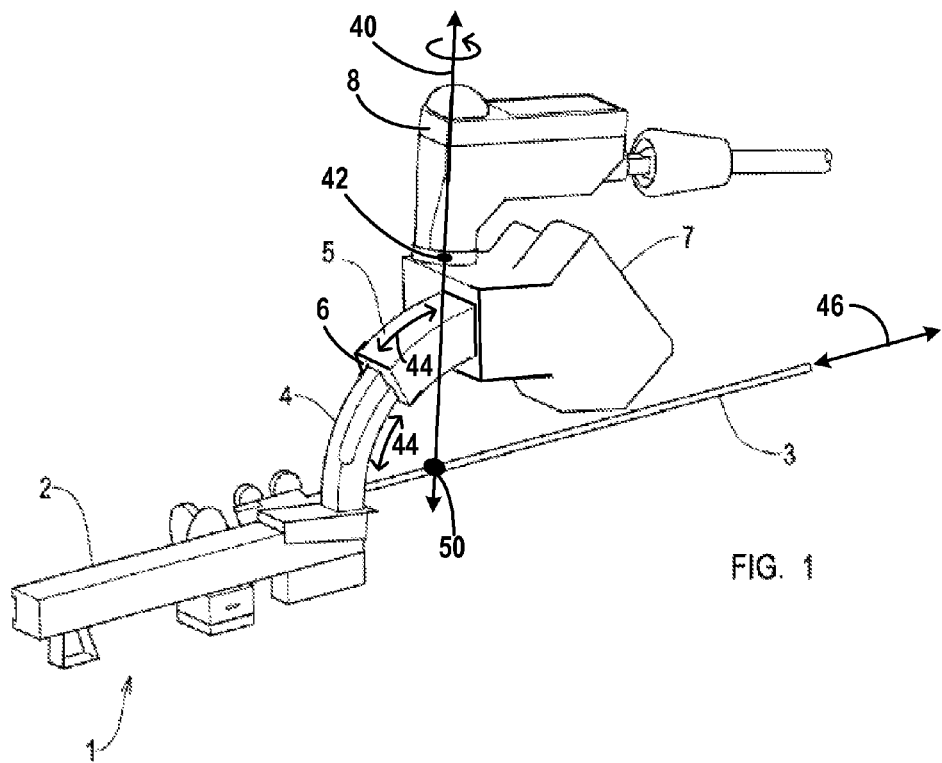
FIG. 1 shows a perspective view of the telescopic drive embodying the present invention.

With reference to FIG. 1, a part of a surgical robot is shown, supporting an endoscope 1. The endoscope 1 comprises an elongate body 2, from which a thin, elongate camera 3 protrudes. Images are collected at the far end of this camera 3, and the camera 3 may also include a light source to illuminate objects within the field of vision of the camera. It will be understood that it is this camera 3 which is inserted into an incision 50 in the patient's body during endoscopic surgery, to allow the surgeon to inspect a part of the patient's body, or to see the progress of a surgical procedure. The camera 3 may be extended from, or retracted into the housing 2, thus allowing the "zoom" motion of the endoscope 1 along axis 46. It will be understood that this zoom motion does not place any significant stress on the sides of the incision 50.

Images collected by the camera 3 are transmitted from the endoscope 1 to a remote location, where, for example, they may be viewed by a surgeon on a screen during surgery. This transmission may take place wirelessly, or by any other suitable means.

The endoscope 1 is supported by an outer arm 4, which takes the form of a sturdy, planar strip whose shape describes a section of arc having a constant radius of curvature with respect to axis 44. As will be understood from the above, the radius of curvature of the outer arm 4 is centered on a point along the length of the camera 3. It is this point along the length of the camera 3 that will pass through the incision 50 in a patient's body during endoscopic surgery, and hence that will be the focus of motion of the endoscope 1.

The outer arm 4 is, itself, carried by an inner arm 5. The inner arm 5 takes the form of an arcuate sleeve, having the same radius of curvature as the outer arm 4. The inner arm 5 defines an internal passage 6, which is shaped and sized to receive the outer arm 4 slidably. The outer arm 4 may be received telescopically within the sleeve of the inner arm 5, so that when the outer arm 4 is fully retracted into the inner arm 5 the endoscope 1 abuts or lies close to the inner arm 5. The outer arm 4 may, however, be extended from the inner arm 5, so that the endoscope 1 is supported at some distance from the inner arm 5.

The inner arm 5 is supported by a housing 7, which is sufficiently large that the inner arm 5 may be fully or substantially fully retracted into the housing 7.

It will be appreciated that, if the inner arm 5 is fully retracted into the housing 7, and the outer arm 4 is fully retracted into the inner arm 5, the endoscope 1 will abut or lie close to the housing 7. In this position, the elongate camera 3 of the endoscope 1 is at or near one end of its range of movement. The inner arm 5 may be extended from the housing 7, and the outer arm 4 may be extended from the inner arm 5, and in this position the endoscope 1 is at or near the other end of its range of motion.

The housing 7 is supported by a support 8, which allows the housing 7 to be rotated about an axis 40 that passes from a point of support 42 through the incision 50 in the patient's body. This rotation allows the "pan" motion of the endoscope 1 to occur. The support 8 is preferably part of a larger surgical robot (not shown) that supports the endoscope 1 in an appropriate position for a surgical procedure.

It will be appreciated that the provision of a two-stage telescopic arcuate arm 4, 5 can alleviate the problem discussed above. If the inner and outer arms 5, 4 were replaced by one solid arcuate arm, then when the endoscope 1 was at one end of its range of motion in which it was closest to the housing 7, the arcuate arm would protrude from a back end of the housing 7 and would press into the body of the patient. The fact that the outer arm 4 may fit inside the inner arm 5 prevents this from occurring.

In conventional telescopic arrangements of this type, however, one telescopic element is fully extended during a first phase of extension, and motion of this telescopic element then stops while motion of a further telescopic element commences. For instance, in a conventional arrangement of this type, starting from a situation in which both arms 4, 5 were retracted and received within the housing 7, a first step might be to extend the outer arm 4 fully, without extending the inner arm 5. Only once the outer arm 4 had reached the full end of its range of motion, the inner arm 5 would be extended, without further relative motion of the outer arm 4 with respect to the inner arm 5.

For an application such as endoscopic surgery, however, motion of this type is likely to cause problems. At the point where motion of the outer arm 4 ends, and motion of the inner arm 5 commences, there will inevitably be some "jerkiness" or driving the motion discontinuity in the motion of the endoscope 1. Further, the load on the motor will change significantly when both arms 4, 5 need to be driven together, as compared to the situation in which only the outer arm 4 needs to be driven. The speed of motion of the endoscope 1 is therefore likely to be different during the two phases of motion.

To address this problem, in preferred embodiments of the invention the inner and outer arms 4, 5 are geared so that, during tilt motion along axis 44 of the endoscope, both arms 4, 5 advance or retract simultaneously.

For instance, in moving from a situation in which both arms 4, 5 are fully retracted, in advantageous embodiments of the invention both arms 4, 5 are extended at an equal rate, until both arms 4, 5 reach the ends of their respective ranges of motion simultaneously. In other words, when the extension of the outer arm 4 with respect to the inner arm 5 is complete, the extension of the inner arm 5 with respect to the housing 7 will also be complete.

It will be appreciated that, using this technique, there will be no jerkiness or discontinuity when one telescopic element has finished advancing, and motion of another telescopic element begins. Further, the load on the motor will not vary significantly during any stage of the motion, since the same elements are being driven at all stages of motion.

Figure 2:
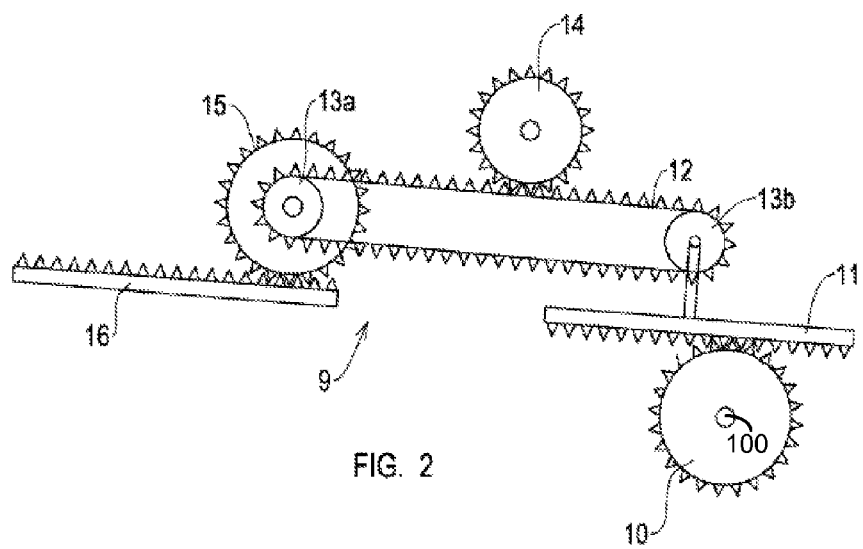
FIG. 2 shows a schematic view of a gearing arrangement for use with the present invention.

FIG. 2 shows one possible gearing system 9 which could be used with the present invention. For clarity the gearing system 9 is shown driving motion in a straight, linear direction, but it will be appreciated that the components may readily be adapted for driving arcuate arms. A toothed main drive wheel 10 is provided, that may be driven directly by the motor 100. The main drive wheel 10 is rotatable, but fixed in position. A first toothed rack 11 is provided in contact with the periphery of the main drive wheel 10, and arranged such that rotation of the main drive wheel 10 will propel the first rack 11 in either a forward or backward direction. The inner arm 5 is connected to the first rack 11, and it will be understood that rotation of the main drive wheel 10 will therefore act to extend or retract the inner arm 5 with respect to the housing 7.

Contained, or substantially contained within the inner arm 5, is a toothed belt 12, which passes around a pair of freely rotatable wheels 13a, 13b. A fixed cog 14 is attached to the housing 7, and which does not rotate. The wheels 13a, 13b are positioned such that, regardless of the position of extension or retraction of the inner arm 5 with respect to the housing 7, the fixed cog 14 is always in contact with a part of the toothed belt 12. It will be understood that the toothed belt 12 therefore extends substantially the entire length of the inner arm 5.

It will be appreciated that, as the inner arm 5 extends from the housing 7, the toothed belt 12 will rotate with respect to the wheels 13a, 13b on which it is mounted. This is because the wheels 13a, 13b will move with respect to the fixed cog 14, whereas the portion of the toothed belt 12 that contacts the fixed cog 14 will not be free to move with respect to the fixed cog 14. The wheel 13a which is closest to the end of the inner arm 5 which is furthest from the housing 7 when inner arm 5 is extended will therefore rotate as the inner arm 5 is extended away from the housing 7.

A secondary drive cog 15 is attached to the axle around which the wheel 13a turns, and this secondary drive wheel 15 is adapted to engage a second rack 16, to which the outer arm 4 is attached. As the secondary drive wheel 15 rotates, the second rack 16, and hence the outer arm 4, may be driven in an extending or retracting motion relative to the inner arm 5.

With reference to the arrangement depicted in FIG. 2, it can be understood that, when the inner arm 5 is driven to extend away from the housing 7, the outer arm 4 will simultaneously be driven to extend away from the inner arm 5. Correspondingly, when the inner arm 5 is driven to retract into the housing 7, the outer arm 5 would be driven to retract into the inner arm 5.

Figure 3:
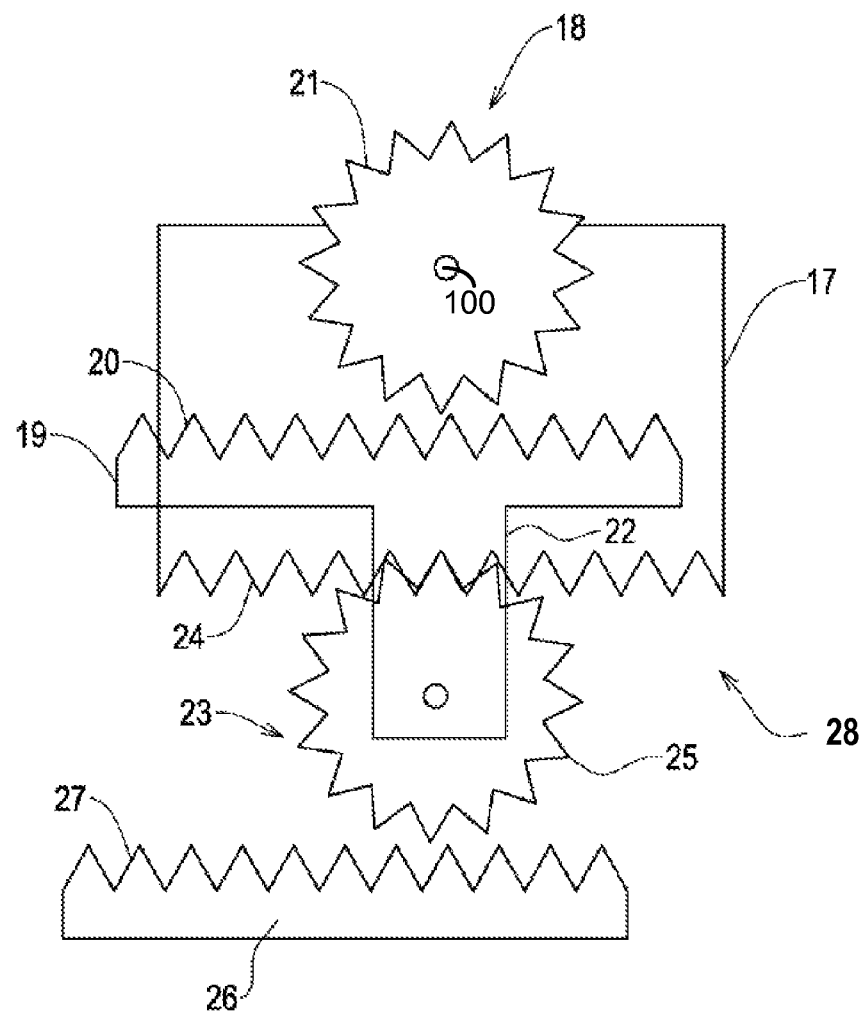
FIG. 3 shows a schematic view of an alternate gearing arrangement for use with the present invention.

Referring to FIG. 3, an alternative gearing system 28 is shown. The alternative gearing system 28 comprises a fixed housing 17, to which a pinion wheel 18 is attached. The pinion wheel 18 may be rotatably driven by a motor 100. A third toothed rack 19 is slidably mounted with respect to the housing 19 so that teeth 20 of the third rack engage with the teeth 21 of the pinion wheel 18. Rotation of the pinion wheel 18 will therefore cause translational motion of the third rack 19 with respect to the housing 17.

The third rack 19 has a protrusion 22 which extends away from the third rack 19, substantially away from the toothed face of the third rack 19. A further pinion wheel 23 is rotatably mounted on the protrusion 22.

An array of teeth 24 are provided on the housing 17, arranged such that the teeth 25 of the further pinion wheel 23 mesh with the array of teeth 24. It will therefore be appreciated that, as the third rack 19 moves with respect to the housing 17, the engagement of the array of teeth 24 that are provided on the housing and the teeth 25 of the further pinion wheel 23 will cause the further pinion wheel 23 to rotate.

Finally, a fourth toothed rack 26 is slidably mounted with respect both to the housing 17 and to the third rack 19, and is arranged so that teeth 27 of the fourth rack engage with the teeth 25 of the further pinion wheel 23. It will be appreciated that rotation of the further pinion wheel 23 will therefore cause a translational motion of the fourth rack 26 with respect to the third rack 19. Thus, rotation of the pinion wheel 23 will cause translational motion of the third rack 19 with respect to the housing 17; and motion of the fourth rack 26 with respect to the third rack 19.

It will be understood that the further gearing system 28 could be used in connection with the invention, with, for example, motion of the inner arm 4 being controlled by movement of the third rack 19, and movement of the outer arm 5 being controlled by a motion of the fourth rack 26.

The skilled person will, however, realize that many other types of drive arrangements are possible, and the invention is not limited to the arrangement described above.

Figure 4:
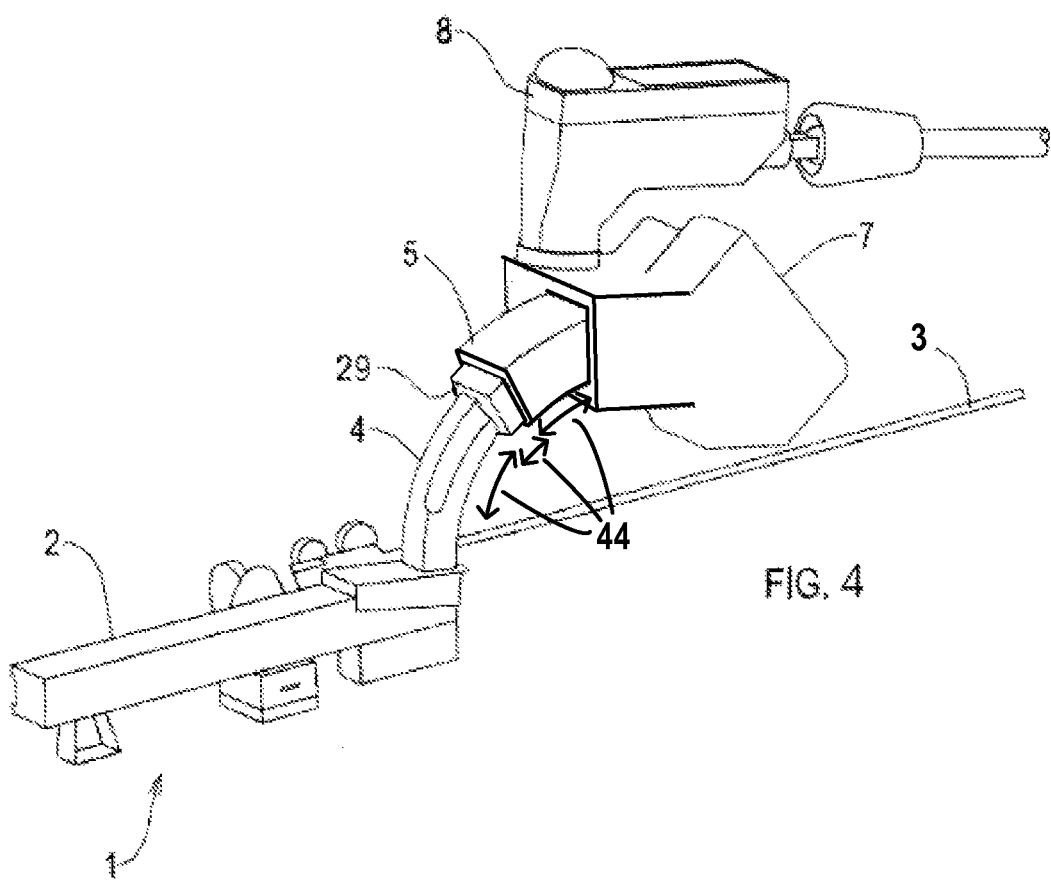
FIG. 4 shows a perspective view of a telescopic drive embodying the present invention having an additional third telescoping stage.

Whilst the above example is given with two telescopic elements, the skilled person will readily envisage that a similar arrangement could be put in place with three or more telescopic stages. FIG. 4 shows an example telescopic drive having a third telescopic stage 29 in addition to inner and outer arms 5, 4.

Further, while the above-described embodiment includes an arcuate telescopic arm, it will be appreciated that the invention may equally apply to a linear telescopic drive, or indeed any other type of telescopic drive.

It will be appreciated that the present invention provides a simple and robust solution to the problems described above, and will find utility in many fields.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

We claim:

1. A telescopic drive device of a device for holding an endoscopic surgical instrument, the telescopic drive device comprising:
    a support;
    a first telescopic stage carried by the support, the first telescopic stage being able to perform a first motion with respect to the support;
    a second telescopic stage, which is able to perform a second motion with respect to the first telescopic stage, the second telescopic stage being carried by the first telescopic stage, wherein the first motion and the second motion are telescopic and occur along the same arcuate path; and
    a drive system including a motor, the motor being configured to drive both the first and second motions, wherein the first telescopic stage and the second telescopic stage are each geared such that gearing of the first telescopic stage is in contact with gearing of the second telescopic stage so that the first telescopic stage performs the first motion and the second telescopic stage simultaneously performs the second motion, wherein each of the telescopic stages is arcuate in shape.

2. The telescopic drive device of claim 1, wherein each of the telescopic stages has a range of motion with respective ends, and wherein, starting from a position in which both telescopic stages are at one end of their respective ranges of motion, the gearing of first and second telescopic stages allow the telescopic stages to reach the ends of their respective ranges of motion substantially simultaneously.

3. The telescopic drive device of claim 1, further comprising a third telescopic stage being adapted to perform third motion with respect to the second telescopic stage, and wherein the drive arrangement is configured to drive the third motion simultaneously with the first and second motions, the third telescopic stage being carried by the first telescopic stage and carrying the second telescopic stage.

4. The telescopic drive device of claim 1, further comprising an endoscopic surgical instrument which is supported by the second telescopic stage of the telescopic drive device.

5. The telescopic drive device of claim 4, being operable to move the endoscopic surgical instrument such that the movement is centered around a point, the endoscopic surgical instrument being supported by the second telescopic stage of the telescopic drive device.

6. The telescopic drive device of claim 5, the endoscopic surgical instrument being moveable in a tilt movement with respect to the point.

7. The telescopic drive device of claim 5, wherein the endoscopic surgical instrument is moveable along a plurality of axes to describe motion that is confocal about the point.

8. The telescopic drive device of claim 5, wherein the endoscopic surgical instrument is moveable around a plurality of axes to describe motion that is confocal about the point.

9. The telescopic drive device of claim 1, wherein the device for holding an endoscopic surgical instrument is a robot.

10. A telescopic drive device of a device for holding an endoscopic surgical instrument, the telescopic drive device comprising:
    a support;
    a first telescopic stage carried by the support, the first telescopic stage being able to perform a first motion with respect to the support;
    a second telescopic stage, which is able to perform a second motion with respect to the first telescopic stage, the second telescopic stage being carried by the first telescopic stage, wherein the first motion and the second motion are telescopic and occur along the same arcuate path; and
    a drive system including a motor, the motor being configured to drive both the first and second motions, wherein the first telescopic stage and the second telescopic stage are each geared such that gearing of the first telescopic stage is in contact with gearing of the second telescopic stage so that the first telescopic stage performs the first motion and the second telescopic stage simultaneously performs the second motion, wherein the telescopic drive device is operable to support an endoscopic surgical instrument and the first and second motions are operable to move the endoscopic surgical instrument such that the movement is centered around a point.

11. The telescopic drive device of claim 10, wherein the gearing of the first telescopic stage and the second telescopic stage allow the first motion and the second motion to occur at an equal rate.

12. A method of driving a device for holding an endoscopic surgical instrument, the method comprising:
    providing a support;
    performing a first motion by a first telescopic stage carried by the support, the first motion occurring with respect to the support;
    performing a second motion by a second telescopic stage with respect to the first telescopic stage, the second telescopic stage being carried by the first telescopic stage, wherein the first motion and the second motion are telescopic and occur along the same arcuate path; and
    driving, with aid of a drive system including a motor, the first and second motions so that the first telescopic stage performs the first motion and the second telescopic stage performs the second motion simultaneously, wherein the first and second telescopic stages are arcuate in shape and interconnected by rack and pinion gearing in contact with the first and second telescopic stages, and the motor drives both the first and second motions.

13. The method of claim 12, wherein the first motion and the second motion occur simultaneously at the same rate.

14. The method of claim 12, wherein each of the first telescopic stage and the second telescopic stage has a range of motion with respective ends, and further comprising driving the first motion and the second motion starting from a position in, which the first telescopic stage and the second telescopic stage are at one end of their respective ranges of motion to reach the other ends of their respective ranges of motion substantially simultaneously.

15. The telescopic drive device of claim 1, wherein the gearing of the first telescopic stage and the second telescopic stage comprise rack and pinion gearing.

16. The telescopic drive device of claim 15, wherein the rack and pinion gearing comprises:
    a pinion wheel attached to a fixed housing of the support, the pinion wheel being rotatably drivable by the motor, the fixed housing including an array of teeth;
    a first toothed rack slidably mounted with respect to the fixed housing such that teeth of the first toothed rack engage teeth of the pinion wheel and rotation of the pinion wheel causes translational movement of the first toothed rack with respect to the fixed housing, wherein the first toothed rack is coupled for movement with the first telescopic stage and the first toothed rack has a protrusion which extends away from the first toothed rack, substantially away from a toothed face of the first toothed rack;
    a further pinion wheel rotatably mounted on the protrusion, such that teeth of the further pinion wheel mesh with the array of teeth of the fixed housing and movement of the first toothed rack with respect to the fixed housing and the engagement of the array of teeth of the fixed housing and the teeth of the further pinion wheel causes the further pinion wheel to rotate; and
    a second toothed rack slidably mounted with respect to both the fixed housing and the first toothed rack, the second toothed rack being coupled for movement with the second telescopic stage and being arranged such that teeth of the second toothed rack engage teeth of the further pinion wheel, wherein rotation of the further pinion wheel causes translational motion of the second toothed rack with respect to the first toothed rack, wherein the first motion is controlled by movement of the first toothed rack and the second motion is controlled by movement of the second toothed rack.

17. The telescopic drive device of claim 10, wherein the gearing of the first telescopic stage and the second telescopic stage comprise rack and pinion gearing.

18. The telescopic drive device of claim 17, wherein the rack and pinion gearing comprises:
    a pinion wheel attached to a fixed housing of the support, the pinion wheel being rotatably drivable by the motor, the fixed housing including an array of teeth;
    a first toothed rack slidably mounted with respect to the fixed housing such that teeth of the first toothed rack engage teeth of the pinion wheel and rotation of the pinion wheel causes translational movement of the first toothed rack with respect to the fixed housing, wherein the first toothed rack is coupled for movement with the first telescopic stage and the first toothed rack has a protrusion which extends away from the first toothed rack, substantially away from a toothed face of the first toothed rack;

a further pinion wheel rotatably mounted on the protrusion, such that teeth of the further pinion wheel mesh with the array of teeth of the fixed housing and movement of the first toothed rack with respect to the fixed housing and the engagement of the array of teeth of the fixed housing and the teeth of the further pinion wheel causes the further pinion wheel to rotate; and a second toothed rack slidably mounted with respect to both the fixed housing and the first toothed rack, the second toothed rack being coupled for movement with the second telescopic stage and being arranged such that teeth of the second toothed rack engage teeth of the further pinion wheel, wherein rotation of the further pinion wheel causes translational motion of the second toothed rack with respect to the first toothed rack, wherein the first motion is controlled by movement of the first toothed rack and the second motion is controlled by movement of the second toothed rack.

19. The method of claim 12, wherein driving the first and second motions comprises:

driving rotation of a pinion wheel attached to a fixed housing of the support, the pinion wheel being rotatably drivable by the motor, the fixed housing including an array of teeth;

moving a first toothed rack, which is slidably mounted with respect to the fixed housing such that teeth of the first toothed rack engage teeth of the pinion wheel, by the rotation of the pinion wheel to cause translational movement of the first toothed rack with respect to the fixed housing, wherein the first toothed rack is coupled for movement with the first telescopic stage and the first toothed rack has a protrusion which extends away from the first toothed rack, substantially away from a toothed face of the first toothed rack;

rotating a further pinion wheel, which is rotatably mounted on the protrusion such that teeth of the further pinion wheel mesh with the array of teeth of the fixed housing, by the movement of the first toothed rack with respect to the fixed housing and the engagement of the array of teeth of the fixed housing and the teeth of the further pinion wheel; and moving a second toothed rack, which is slidably mounted with respect to both the fixed housing and the first toothed rack, the second toothed rack being coupled for movement with the second telescopic stage and being arranged such that teeth of the second toothed rack engage teeth of the further pinion wheel, by the rotation of the further pinion wheel to cause translational motion of the second toothed rack with respect to the first toothed rack, wherein the first motion is controlled by movement of the first toothed rack and the second motion is controlled by movement of the second toothed rack.

\* \* \* \* \*